(12) United States Patent
Ooshima et al.

(10) Patent No.: US 6,181,369 B1
(45) Date of Patent: Jan. 30, 2001

(54) VIDEOSCOPE FOR DENTAL OR OTHER USE

(75) Inventors: Kiyoko Ooshima; Hiroshi Atsuta; Shinji Uchida; Hiroyuki Yamakita, all of Osaka (JP)

(73) Assignee: Matsushita Electric Industrial Co., Ltd., Osaka (JP)

(*) Notice: Under 35 U.S.C. 154(b), the term of this patent shall be extended for 0 days.

(21) Appl. No.: 09/001,134

(22) Filed: Dec. 30, 1997

(30) Foreign Application Priority Data

Jan. 9, 1997 (JP) .................................................. 9-002030
Mar. 21, 1997 (JP) .................................................. 9-068340

(51) Int. Cl.[7] .............................. H04N 7/18; A61B 1/05; A61B 1/02
(52) U.S. Cl. ............................... 348/66; 348/68; 433/29; 600/182
(58) Field of Search ...................... 348/66, 68; 433/29; 600/160, 182; H04N 7/18

(56) References Cited

U.S. PATENT DOCUMENTS

| | | | | |
|---|---|---|---|---|
| 5,702,249 | * | 12/1997 | Cooper | 433/29 |
| 5,745,165 | * | 4/1998 | Atsuta et al. | 348/65 |
| 5,771,067 | * | 6/1998 | Williams et al. | 348/66 |
| 6,002,424 | * | 12/1999 | Rapa et al. | 348/66 |
| 6,007,333 | * | 12/1999 | Callan et al. | 433/29 |
| 6,095,811 | * | 8/2000 | Stearns | 433/29 |
| 6,116,899 | * | 9/2000 | Takeuchi | 433/29 X |

FOREIGN PATENT DOCUMENTS

| | | |
|---|---|---|
| 62-246347 | 10/1987 | (JP) . |
| 4-176436 | 6/1992 | (JP) . |
| 4-285525 | 10/1992 | (JP) . |

* cited by examiner

Primary Examiner—Howard Britton
(74) Attorney, Agent, or Firm—Merchant & Gould P.C.

(57) ABSTRACT

A videoscope for dental or oral use comprises a grip portion, an insert portion, a light window formed in the wall of the insert portion for illuminating an object, an acceptance window formed in the wall of the insert portion for receiving reflected light from the object, an image sensor disposed in the tip of the insert portion for receiving the light from the object to generate an electric signal corresponding to the object image, a light source disposed in the grip portion, and a light guide for guiding light rays from the light source to the light window. The light guide is made of a transparent plastic material. The light guide has a condensing portion that condenses the light rays emitted by the light emitting member, a guiding portion in which the light rays can propagate by total reflection, and a shedding portion that sheds the propagated light rays through the light window.

22 Claims, 11 Drawing Sheets

VIDEOSCOPE FOR DENTAL OR OTHER USE

BACKGROUND OF THE INVENTION

This invention relates to a videoscope employing an image sensor such as a charge coupled device (CCD), and especially relates to a dental scope used for a dental or oral use.

Recently, such a videoscope has been used for an examination or a medical care of an oral cavity in a dental clinic or in oral surgery. One type of such videoscope employs an optical fiber for guiding light rays as disclosed in Japanese laid open patent applications (Tokukaihei) 4-176436 and 4-285525, for example. Another type disclosed in Japanese laid open patent application (Tokukaisho) 62-246347 uses an optical fiber for guiding an image of the object to the image sensor such as CCD. The videoscope disclosed in Tokukaihei 4-176436 uses an optical system including lenses for guiding an image of the object to the image sensor.

Such a videoscope is required to be easy to handle with one hand, have a high quality image and an inexpensive price for wide use.

The prior art disclosed in Tokukaihei 4-176436 has an optical fiber for guiding light rays. This optical fiber should have a complicated shape fitting to a narrow space inside the videoscope, which also contains lenses and prisms for condensing or dispersing light rays. However, since an optical fiber is hard to bend in a small angle and is easy to break, it can hardly extend to the tip inner portion. It is also difficult to decrease the number of the components.

The videoscope of the prior art has another disadvantage in that it is not easy to handle since it has an optical fiber connecting a grip portion of the videoscope and an external light source box, in addition to an electric cable connecting the grip portion of the videoscope and an external video circuit. The optical fiber and the electric cable can be integrated into a cord in recent technology, but it is not enough to improve the difficulty in handling the videoscope.

Moreover, the videoscope of the prior art needs a long optical path including lenses or an optical fiber for transmitting a light image of the object to an image sensor. This complicated structure makes it difficult to reduce the size and cost of the video scope.

The present invention is aimed at a novel structure of such a videoscope that enables easiness of handling and an inexpensive price.

SUMMARY OF THE INVENTION

A videoscope of the present invention comprises a grip portion at a proximal end to be held by an operator; an insert portion at a distal end to enter the oral cavity or other objects; a light window formed in the wall of the insert portion for illuminating an object; an acceptance window formed in the wall of the insert portion for receiving reflected light from the object; an image sensor disposed in the tip of the insert portion for receiving the light from the object to generate an electric signal corresponding to the object image; a light emitting member disposed in the grip portion; and a light guide for guiding light rays from the light emitting member to the light window. The light guide has a condensing portion that condenses the light rays emitted by the light emitting member, a guiding portion in which the light rays can propagate by total reflection, and a shedding portion that sheds the propagated light rays through the light window.

According to the above mentioned structure, since the image sensor is disposed in the tip of the insert portion, it can receive the light rays containing the image of the object directly without an optical fiber or other optical guide members. Light rays for illuminating the object are guided by the light guide from the light emitting member in the grip portion to the light window in the tip of the insert portion. The structure of the present invention is simpler and lower in cost than that of the prior art. It enables the videoscope to be compact and easy to handle since it does not need an optical fiber extending to the outside of the videoscope.

It is preferable that the videoscope has a plurality of light windows formed in the wall of the insert portion for illuminating an object, the light emitting member includes a light source and a concave mirror that reflects the light rays from the light source in the direction toward the tip of the insert portion, and the light guide has a plurality of shedding portions, a plurality of guiding portions and a condensing portion that condenses the light rays from the light source and the concave mirror to the plurality of guiding portions.

It is also preferable that the videoscope further comprises a video circuit disposed in the grip portion and a mirror disposed between the video circuit and the light emitting member for reflecting the light rays from the light emitting member in the direction toward the tip of the insert portion. The mirror in this structure works not only for condensing the light rays but also as a heat shield for the video circuit when the light has a certain heat that may damage the video circuit.

It is also preferable that the cross section of the insert portion has a substantially oblong profile, and the light window and the acceptance window are formed in the wider side wall of the insert portion.

It is also preferable that the light guide has a recess for receiving a light source such as a lamp, and the condensing portion is formed around the recess. In this structure, the condensing portion of the light guide preferably includes a mirror portion that reflects and condenses light rays from the light source to the direction of the guiding portion. Such a mirror portion can be formed by a metal film evaporated on the surface of the light guide or a reflecting sheet stuck on the surface of the light guide.

It is also preferable that the cross section of the condensing portion of the light guide has a substantially oblong profile, and the mirror portion has different curvatures between the longitudinal direction and its perpendicular direction of the oblong cross section.

It is also preferable that a part of the surface of the condensing portion, which does not satisfy the angular condition for the total reflection of the light rays, has a second mirror portion. This mirror portion also can be formed by a metal film evaporated on the surface of the light guide or a reflecting sheet stuck on the surface of the light guide. The second mirror portion preferably has a zigzag inner surface for reflecting the light rays from the light source back to the light source or the periphery of the light source. The zigzag inner surface preferably has flat faces perpendicular to the direction toward the light source.

It is also preferable that the recess for receiving the light source is formed in the direction perpendicular to the longitudinal axis of the light guide. This structure facilitates setting or replacing of the light source such as a lamp from the side of the light guide.

It is preferable that the light source is a lamp with a filament, the cross section of the guiding portion of the light guide has a substantially oblong profile, and the lamp is set in its position such that the longitudinal direction of the filament is along the longitudinal direction of the cross section profile of the guiding portion. This structure enables an efficient usage of the light from the light source.

It is preferable that the shedding portion of the light guide has an oblique shedding face for illuminating the object efficiently. Alternatively, the shedding portion of the light guide has a shedding face with small prisms that diffuse the light rays for illuminating the object uniformly and mildly.

It is also preferable that the side wall of the insert portion is transparent or semitransparent at least partially, and light rays leaked from the light source or the light guide illuminate the object indirectly through the transparent or semitransparent part of the insert portion.

The present invention may be applied to the videoscope that further comprises an optical fiber for guiding light rays from an external light source box to the light emitting member in the grip portion of the videoscope. In this case, the effect of compact size and low cost of the videoscope can be obtained.

It is also preferable that a second light window is formed in the wall of the grip portion for emitting some light rays from the light emitting member to the object through the second light window. In this structure, the object is illuminated by the light rays shed through the light window in the tip of the insert portion and the light rays shed through the second light window in the grip portion.

It is also preferable that the videoscope further comprises a video circuit board that extends from the inside of the grip portion to the inside tip of the insert portion, and the image sensor is mounted on the distal end of the video circuit board. This structure facilitates assembling and maintenance of the videoscope.

DETAILED DESCRIPTION OF THE PREFERRED EMBODIMENTS (First Embodiment)

Figure 1:
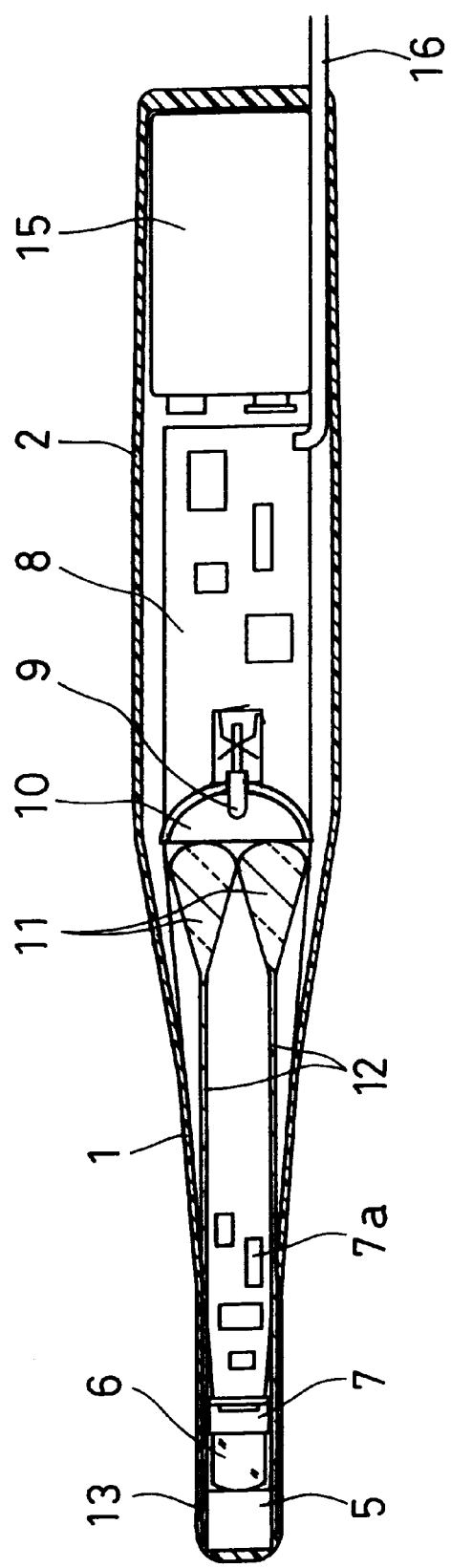
FIG. 1 is a cross section of a videoscope according to a first embodiment of the present invention.
Figure 2:
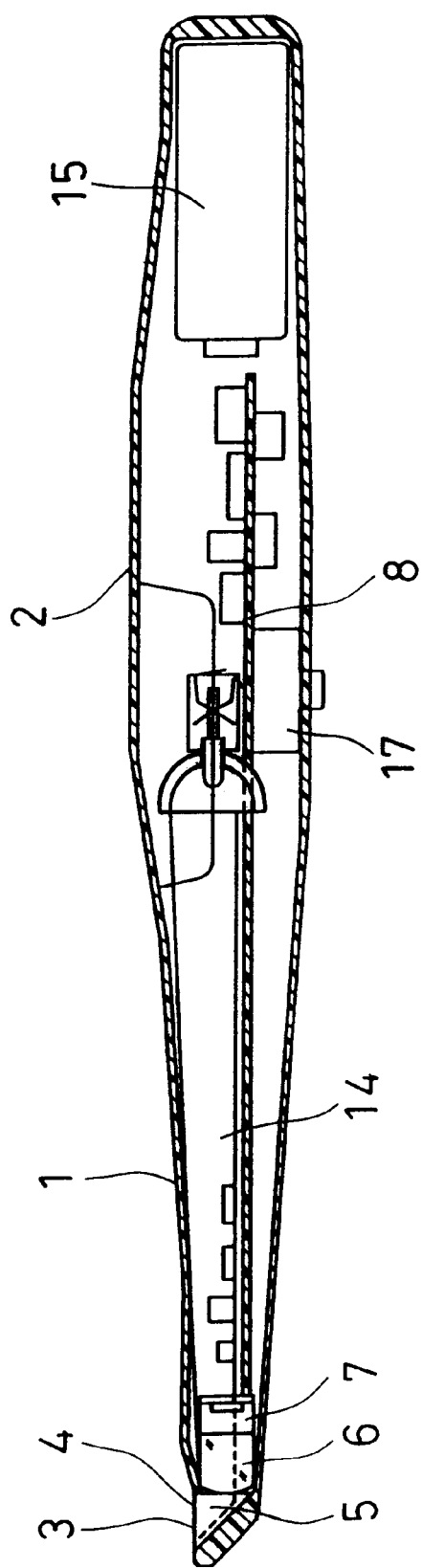
FIG. 2 is another cross section of the videoscope shown in FIG. 1.
Figure 3:
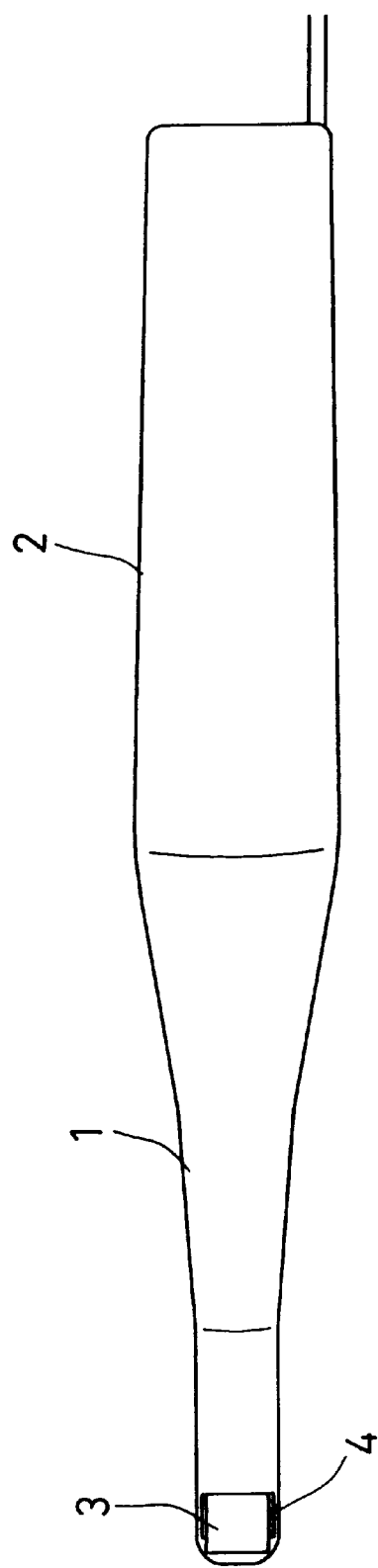
FIG. 3 is an external view of the videoscope shown in FIG. 1.

A videoscope for a dental or oral use according to a first embodiment of the present invention is illustrated in FIGS. 1 to 4. FIGS. 1 and 2 show cross sections, and FIG. 3 shows an external view of the videoscope. In these figures, numeral 1 denotes an insert portion to enter an oral cavity, and 2 is a grip portion to be held by an operator. Two light windows 4 for illuminating an object, i.e., inside of the oral cavity, and an acceptance window 3 for receiving reflected light from the object are formed at the tip of the insert portion. These windows are formed in the wider side wall of the insert portion that has an oblong profile.

A prism 5 is disposed in the tip of the insert portion for directing the reflected light from the object through the acceptance window 3 to CCD unit 7 that is disposed in the tip of the insert portion, too. An object lens 6 is disposed between the prism 5 and the CCD unit 7. Usually, an iris is disposed between the prism 5 and the object lens 6 though it is not shown in the figures. The reflected light rays from the object reach the CCD unit 7 through the acceptance window 3, the prism 5 (and the iris) and the object lens 6.

A video circuit 8 is disposed in the grip portion. The video circuit 8 is formed on a printed wiring board (PWB) that extends from the inside of the grip portion to the inside of the insert portion. The CCD unit 7 and its drive circuit 7a are mounted on the distal end of the PWB of the video circuit 8.

Figure 4A:
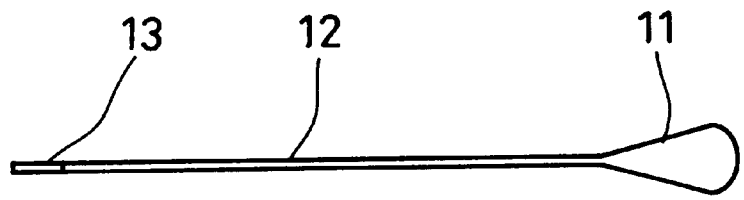
FIGS. 4A and 4B illustrate a light guide used in the videoscope shown in FIG. 1.
Figure 4B:
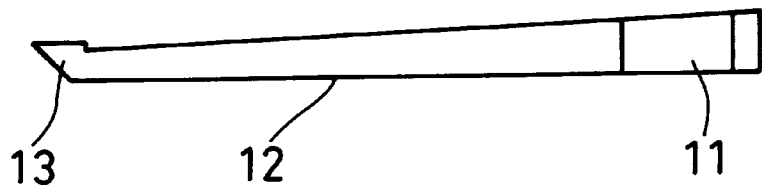

A light source 9 for illuminating the object is disposed in the grip portion 2. Light rays emitted by the light source 9 are directed to the direction of the insert portion by a concave mirror 10 and enter each condensing portion 11 of two light guides 14. Each light guide 14 has the condensing portion 11, a guiding portion 12 and a shedding portion 13 as shown in FIGS. 4A and 4B. The light guide 14 can be made of a transparent plastic such as an acrylic by molding. The light rays that enter the condensing portion 11 of the light guide 14 propagate in a guiding portion 12 and are shed from the shedding portion 13 that is located adjacent to the lighting windows 4.

The condensing portion 11 of the light guide 14 has a shape that is suitable for efficiently condensing the light rays from the light source 9 and the concave mirror 10 and giving them to the guiding portion 12 of the light guide 13. The guiding portion 12 has a thin oblong profile so as to be disposed in a narrow space between the prism 5, the object lens 6, or the CCD unit 7 and the side walls of the insert portion 1. The distal end of the guiding portion 12 has a reflection face angled at 45 degrees to direct the light rays to the shedding portion 13.

The videoscope has a battery 15 in the grip portion 2 for supplying a power to the CCD unit 7 and its drive circuit 7a, the video circuit 8 and the light source 9. An alkaline battery, a lithium battery or a rechargeable battery can be used interchangeably. A video output cable 16 extends from the proximal end of the grip portion 2 for connection with a display such as a monitor TV set. The light source 9 is a halogen lamp, for example, and preferably can be exchanged easily. The light source 9, the CCD unit 7 and its drive circuit 7a and the video circuit 8 are turned on and off by switches arranged on the grip portion though they are not shown in the figures.

As explained above, this videoscope includes two light guides made of a transparent plastic material having a condensing portion, a guiding portion and a shedding portion. Therefore this videoscope can be assembled easily in a low cost compared with that of the prior art while maintaining a good quality image. In addition, since the light rays propagate inside the light guide, the heat of the light rays hardly influence the CCD unit and its drive circuit. The heat of the light rays also does not influence the video circuit since the concave mirror shields the video circuit from heat of the light rays.

Moreover, since the CCD unit is disposed in the tip of the insert portion, an optical fiber or other means for transmitting the image from the object to the CCD unit can be eliminated without deterioration of the image quality. Mounting the CCD unit, its drive circuit and the video circuit on the single PWB facilitates assembling of the videoscope as well as adjusting electric characteristics.

In addition, the videoscope of this embodiment is easy to handle since only a thin video cable is extended from the proximal end of the grip portion and the insert portion can be thin enough to move in the mouth cavity.

(Second Embodiment)

Figure 5:
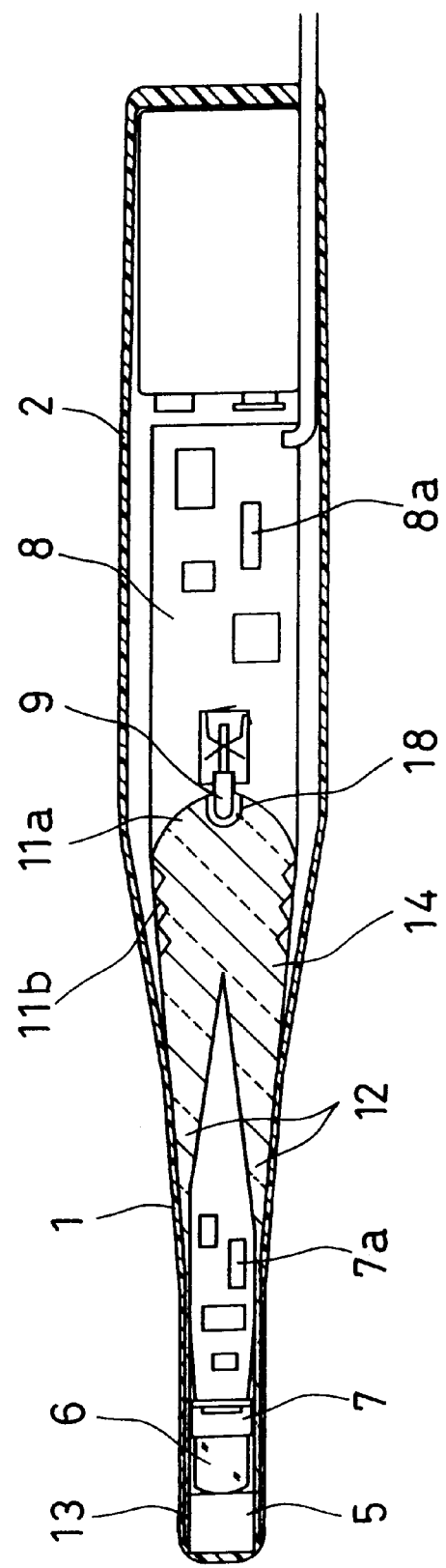
FIG. 5 is a cross section of a videoscope according to a second embodiment of the present invention.
Figure 6:
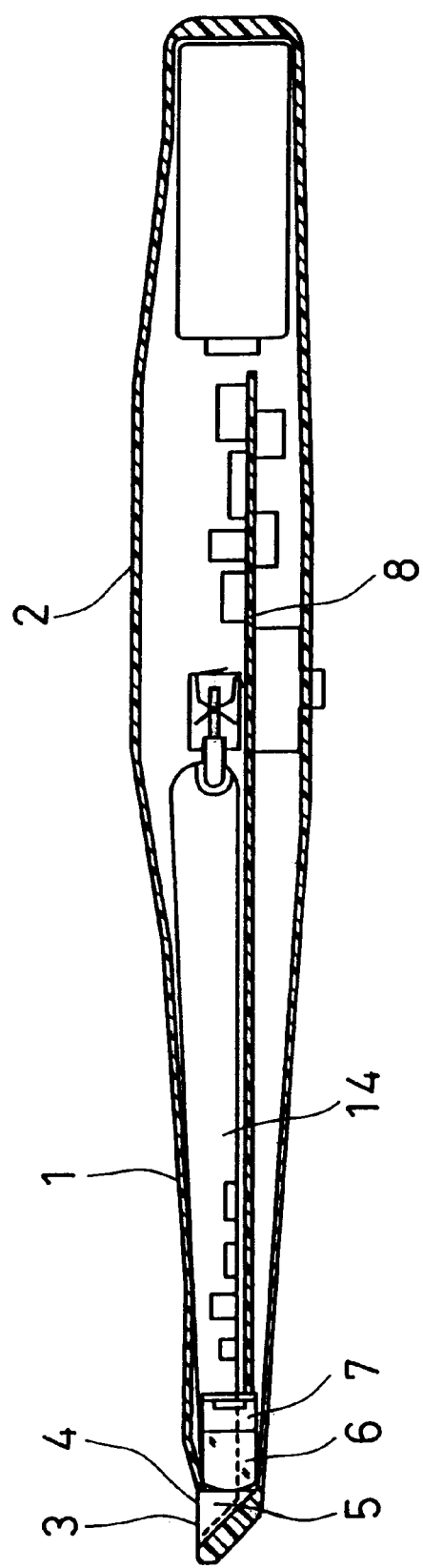
FIG. 6 is a cross section of a videoscope according to a second embodiment of the present invention.

FIGS. 5–7 illustrate a second embodiment of the present invention. In this embodiment, the light guide 14 has a recess 18 for receiving a light source 9, and a concave mirror portion 11a for reflecting light rays from the light source 9 in the direction of the insert portion 1. The light guide 14 also has a zigzag mirror portion 11b for reflecting the light rays from the light source 9 back to a periphery of the light source 9. The reflected light rays reach the periphery of the light source and are reflected again by the mirror portion 11a to go to direction toward the insert portion 1. If there is not such a zigzag mirror portion 11b in this area, the light rays may leak out of the light guide 14 through the area since the area does not satisfy the angular condition for the total reflection of the light rays.

The light rays from the light source 9 or the mirror portion 11a directed to the insert portion 1 are condensed and enter two guiding portions 12 of the light guide 14. The light rays propagate in the guiding portion 12, reach the shedding portion 13 disposed adjacent to the light window 4, and go out of the shedding portion 13 to illuminate the object.

Figure 7A:
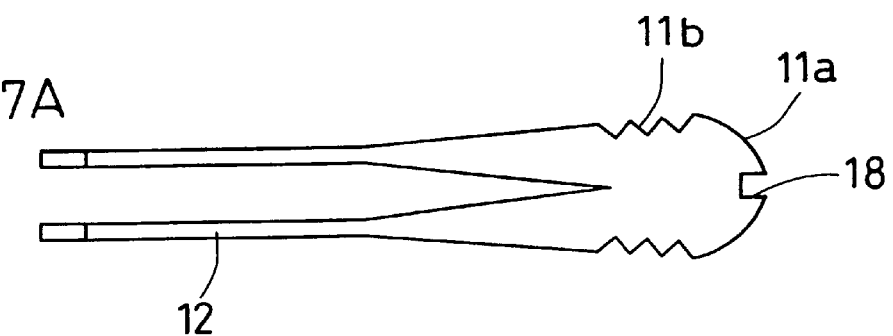
FIGS. 7A and 7B illustrate a light guide used in the videoscope shown in FIG. 6.
Figure 7B:
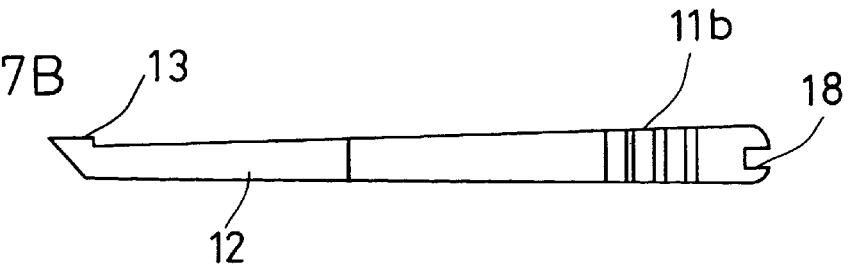

The light guide 13 in this embodiment has two shedding portions 13 and two guiding portions 12 as shown in FIGS. 7A and 7B though they can be single. The light guide 14 having two shedding portions 13 and two guiding portions 12 is made as one unit by molding for example. Alternatively, it can be made by bonding two parts, each of which has one shedding portion and one guiding portion.

The concave mirror portion 11a and the zigzag mirror portion 11b are formed by a metal film, e.g., an aluminum film, which is evaporated on the surface of the light guide for a high reflection rate. Alternatively, the mirror portions can be formed by sticking a reflecting sheet on the surface of the light guide. This method is less expensive than the metal film evaporation.

As shown in FIGS. 7A and 7B, the condensing portion surrounded by the mirror portions 11a and 11b has an oblong profile, i.e., an oblong cross section in the plane perpendicular to the longitudinal axis of the light guide 14. The concave mirror portion 11a has two different curvatures between the longitudinal direction and its perpendicular direction of the oblong cross section for condensing the light rays efficiently.

The zigzag mirror portion 11b, as mentioned above, reflects the light rays from the light source 9 to the periphery of the light source. Otherwise, a lot of light rays may leak out of the light guide when the angle condition for the total reflection is not satisfied. The light rays reflected by the zigzag mirror portion 11b also raise a temperature around the light source such as a halogen lamp and enhance a luminous efficiency of the lamp. The zigzag mirror portion 11b has flat faces perpendicular to the direction toward the light source as shown in FIG. 7A. The flat face is easier to form than a curved face though the curved face is preferable for condensing the reflected light rays to the light source and its close periphery. The zigzag mirror portions 11b are formed on the narrower sides of the condensing portion of the light guide as shown in FIGS. 7A and 7B. However, they can also be formed on the wider sides.

Figures 8A, 8B:
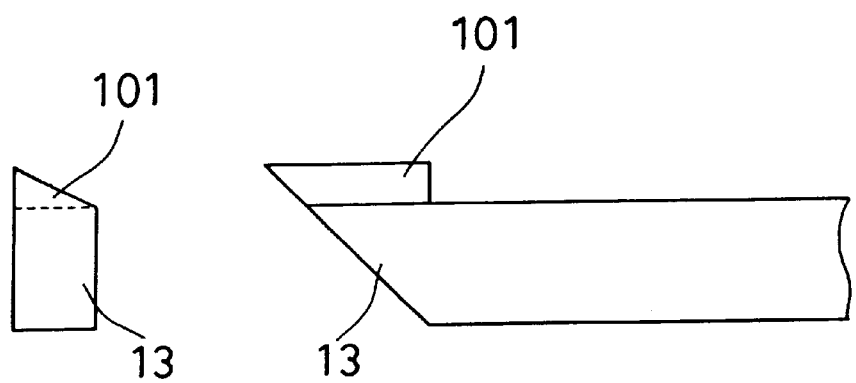
FIGS. 8A and 8B illustrate an example of the shedding face of the light guide shown in FIGS. 7A and 7B.
Figures 9A, 9B:
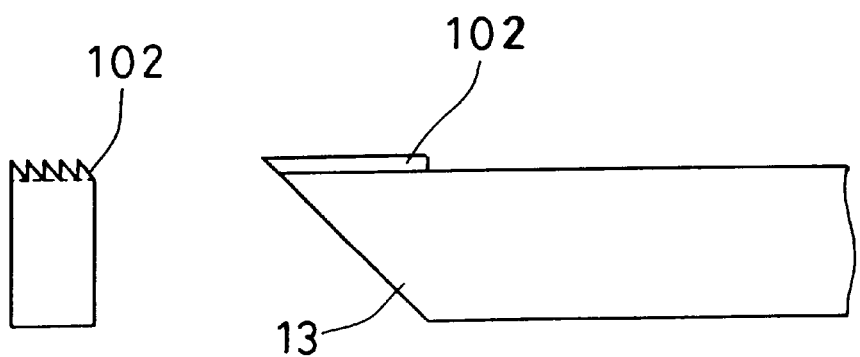
FIGS. 9A and 9B illustrate another example of the shedding face of the light guide shown in FIGS. 7A and 7B.

The shedding portion of the light guide is also optimized for illuminating the object uniformly and mildly. As shown in FIGS. 8A and 8B, a prism portion 101 having an oblique shedding face is bonded to the top face of the shedding portion 13 for illuminating the object efficiently. Alternatively, as shown in FIGS. 9A and 9B, the shedding portion 13 of the light guide 14 may have a shedding face with small prisms 102. Alternatively, the shedding portion 13 of the light guide 14 may have a rough shedding face that diffuses the light rays for illuminating the object uniformly and mildly.

In this embodiment, the recess 18 for receiving the light source 9 is formed in the direction along the longitudinal axis of the light guide 14. However, it is preferable that the recess 18 for receiving the light source 9 is formed in the direction perpendicular to the longitudinal axis of the light guide 14 to facilitate setting or replacing the light source 9 such as a lamp from the side of the light guide 14. For example, the light guide 14 and the video circuit PWB 8 can be assembled easily after mounting the lamp 9 directly on the video circuit PWB 8.

In another variation of the present embodiment, the light source is a lamp with a filament, and the lamp is set in its position such that the longitudinal direction of the filament is along the longitudinal direction of the cross section profile of the guiding portion. This structure enhances an efficiency of the light transmission from the light source to the guiding portion of the light guide.

(Third Embodiment)

Figure 10:
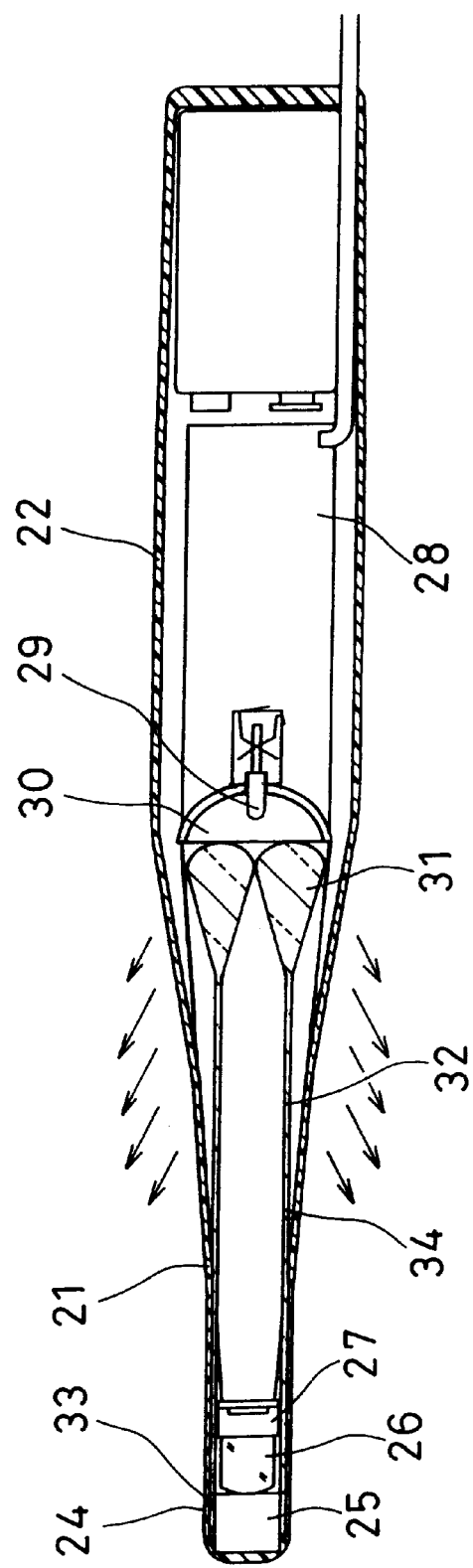
FIG. 10 is a cross section of a videoscope according to a third embodiment of the present invention.

FIG. 10 shows a cross section of a videoscope according to a third embodiment of the present invention. In this figure, numeral 21 is an insert portion made of a transparent or semitransparent plastic material such as an acrylic resin or an ABS resin. Numeral 22 is a grip portion. The insert portion contains a prism 25, an object lens 26 and a CCD unit 27. The grip portion 22 contains a video circuit 28 and a light source 29. The light rays emitted by the light source 29 are directed to the insert portion 21 by a concave mirror 30, enter each condensing portion 31 of two light guides 34, propagate in a guiding portion 32 of the light guide, and go out of the shedding portion 33 located adjacent to a light window 24. Some of the light rays from the light source 29, the concave mirror 30 or the light guide leak out of the videoscope through the transparent or semitransparent side wall of the insert portion 21. The leaked light rays illuminate the object indirectly and help the direct illumination from the light window 24 for obtaining a brighter and more uniform image of the object. Other structure and functions are the same as the first embodiment shown in FIGS. 1 and 2.

(Fourth Embodiment)

Figure 11A:
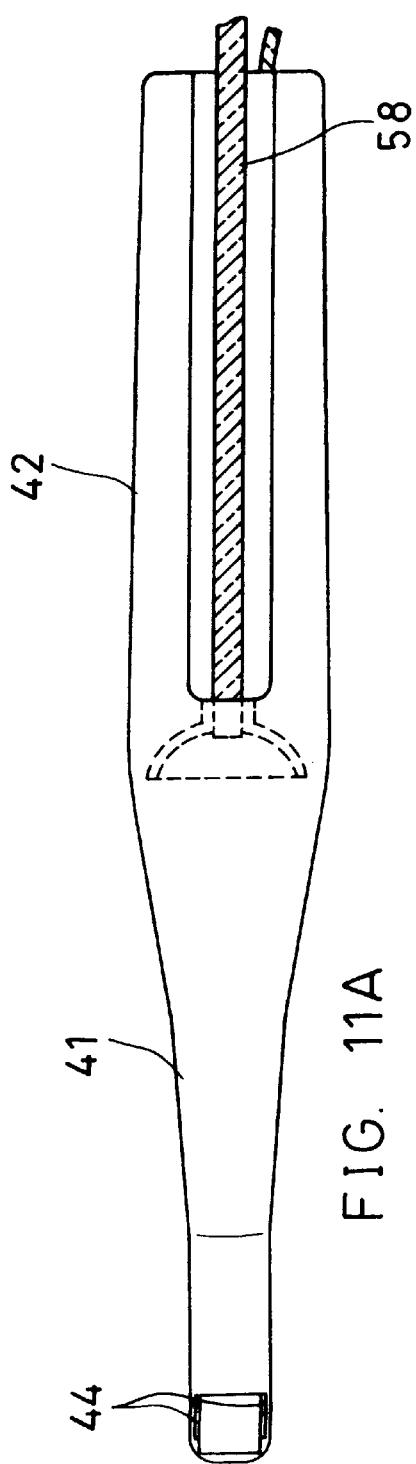
FIGS. 11A and 11B illustrate a videoscope according to a fourth embodiment of the present invention.
Figure 11B:
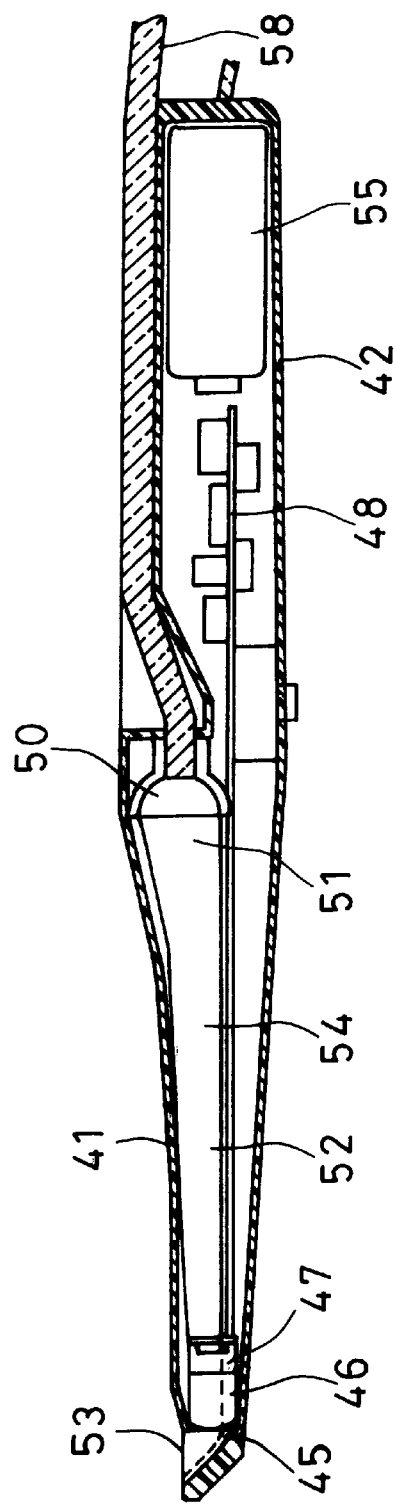

FIGS. 11A and 11B show a fourth embodiment of the present invention. In these figures, numeral 41 is an insert portion, and 42 is a grip portion. The insert portion contains a prism 45, an object lens 46 and a CCD unit 47. The grip portion 42 contains a video circuit 48, a battery 55, a concave mirror 50 and an optical fiber 58. The optical fiber 58 is connected to the concave mirror and guides light rays from an external light source box to the concave mirror 50. The light rays emitted from the end of the optical fiber enter a condensing portion 51 of the light guide 54, propagate in a guiding portion 52 of the light guide 54, and go out of the shedding portion 53 located adjacent to a light window 44.

In this embodiment too, the light guide 54 can contribute to reductions of size and cost of the videoscope without degrading the image quality.

(Fifth Embodiment)

Figure 12:
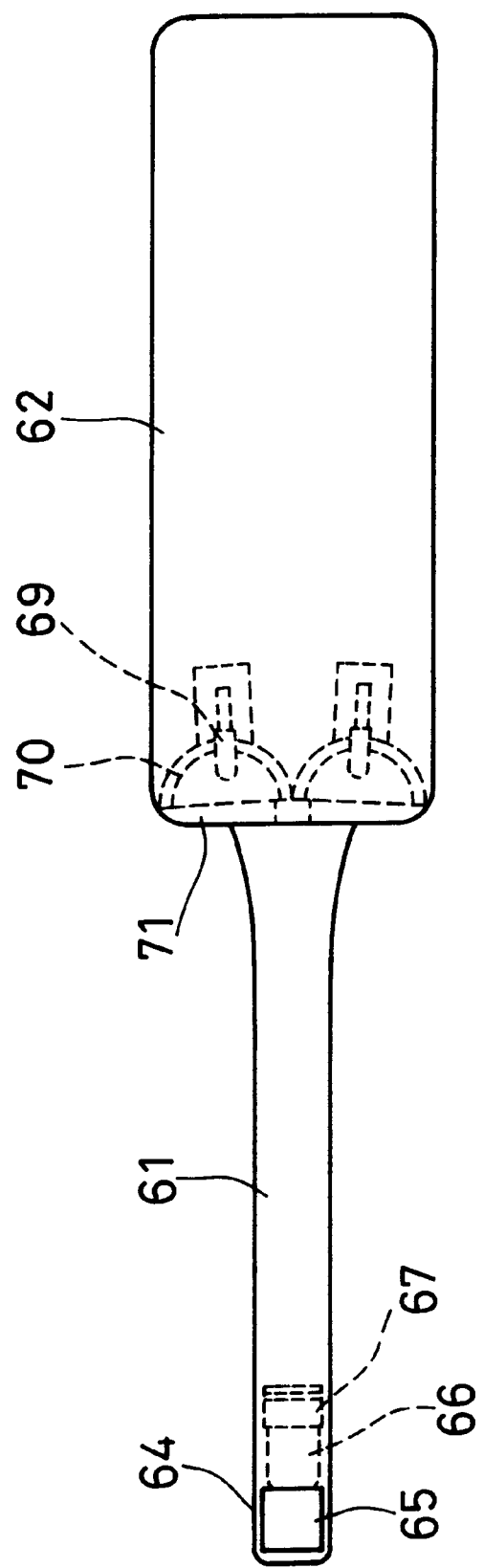
FIG. 12 illustrates a videoscope according to a fifth embodiment of the present invention.

FIG. 12 shows a fifth embodiment of the present invention. In this figure, numeral 61 is an insert portion, and 62 is a grip portion. Adding to the first light window 64 formed on the tip of the insert portion, a second light window 71 is formed in the wall of the grip portion 62 facing the direction toward the insert portion 61. The second light window is an opening or a transparent or semitransparent wall. Some part of light rays emitted by light source 69 and reflected by the concave mirror 70 goes out of the videoscope through the second light window 71 for illuminating the object. Another part of the light rays emitted by the light source 69 and reflected by the concave mirror 70 is guided to the tip of the insert portion 61 in the same way as the above-mentioned embodiments. The light rays shed through the first light window 64 illuminate the object in cooperation with the light rays shed through the second light window 71.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, and all changes that come within the meaning and range of equivalency of the claims are intended to be embraced therein.

What is claimed is:

1. A videoscope for taking an image of an oral cavity or other objects, comprising:
   a grip portion at a proximal end to be held by an operator;
   an insert portion at a distal end to enter the oral cavity or other objects, the portion having a wall and a tip;
   a light window formed in the wall of the insert portion for illuminating an object;
   an acceptance window formed in the wall of the insert portion for receiving reflected light from the object;
   an image sensor disposed in the tip of the insert portion for receiving the light from the object to generate an electric signal corresponding to the object image;
   a light emitting member disposed in the grip portion; and
   a light guide for guiding light rays from the light emitting member to the light window, the light guide having a condensing portion that condenses the light rays emitted by the light emitting member, a guiding portion in which the light rays can propagate by total reflection, and a shedding portion that sheds the propagated light rays through the light window.

2. The videoscope according to claim 1, wherein the videoscope has a plurality of light windows formed in the wall of the insert portion for illuminating an object, the light emitting member includes a light source and a concave mirror that reflects the light rays from the light source in the direction of the tip of the insert portion, and the light guide has a plurality of shedding portions, a plurality of guiding portions and a condensing portion that condenses the light rays from the light source and the concave mirror to the plurality of guiding portions.

3. The videoscope according to claim 1, further comprising a video circuit disposed in the grip portion and a mirror disposed between the video circuit and the light emitting member for reflecting the light rays from the light emitting member in the direction of the tip of the insert portion.

4. The videoscope according to claim 1, wherein the cross section of the insert portion has a substantially oblong profile, and the light window and the acceptance window are formed in the wider side wall of the insert portion.

5. The videoscope according to claim 1, wherein the light guide has a recess for receiving a light source, and the condensing portion is formed around the recess.

6. The videoscope according to claim 5, wherein the condensing portion of the light guide includes a mirror portion that reflects and condenses light rays from the light source to the direction of the guiding portion.

7. The videoscope according to claim 6, wherein the mirror portion is formed by a metal film evaporated on the surface of the light guide.

8. The videoscope according to claim 6, wherein the mirror portion is formed by a reflecting sheet stuck on the surface of the light guide.

9. The videoscope according to claim 6, wherein the cross section of the condensing portion of the light guide has a substantially oblong profile, and the mirror portion has different curvatures between the longitudinal direction and its perpendicular direction of the oblong cross section.

10. The videoscope according to claim 6, wherein a part of the surface of the condensing portion that does not satisfy an angular condition for total reflection of the light rays from the light emitting member has a second mirror portion.

11. The videoscope according to claim 10, wherein the second mirror portion is formed by a metal film evaporated on the surface of the light guide.

12. The videoscope according to claim 10, wherein the second mirror portion is formed by a reflecting sheet stuck on the surface of the light guide.

13. The videoscope according to claim 10, wherein the second mirror portion has a zigzag inner surface for reflecting the light rays from the light source in the direction of the periphery of the light source.

14. The videoscope according to claim 13, wherein the zigzag inner surface has flat faces perpendicular to the direction toward the light source.

15. The videoscope according to claim 5, wherein the recess for receiving the light source is formed in the direction perpendicular to the longitudinal axis of the light guide.

16. The videoscope according to claim 5, wherein the light source is a lamp with a filament, the cross section of the guiding portion of the light guide has a substantially oblong profile, and the lamp is set in its position such that the longitudinal direction of the filament is along the longitudinal direction of the cross section profile of the guiding portion.

17. The videoscope according to claim 1, wherein the shedding portion of the light guide has an oblique shedding face.

18. The videoscope according to claim 1, wherein the shedding portion of the light guide has a shedding face with small prisms for diffusing the light rays.

19. The videoscope according to claim 1, wherein the side wall of the insert portion is at least partially transparent or semitransparent at, and light rays leaked from the light source or the light guide illuminate the object indirectly through the transparent or semitransparent part of the insert portion.

20. The videoscope according to claim 1, further comprising an optical fiber for guiding light rays from a light source box outside of the videoscope to the light emitting member in the grip portion of the videoscope.

21. The videoscope according to claim 1, wherein a second light window is formed in the wall of the grip portion for emitting some light rays from the light emitting member to the object through the second light window.

22. The videoscope according to claim 1, further comprising a video circuit board that extends from the inside of the grip portion to the inside tip of the insert portion, the image sensor being mounted on the distal end of the video circuit board.

* * * * *